United States Patent [19]
Bryant et al.

[11] Patent Number: 5,980,525
[45] Date of Patent: Nov. 9, 1999

[54] BONE REAMER WITH IMPELLER

[75] Inventors: Mark Bryant, Auburn; Robert Krebs, Warsaw, both of Ind.

[73] Assignee: Bristol-Myers Squibb Company, New York, N.Y.

[21] Appl. No.: 08/958,242

[22] Filed: Oct. 27, 1997

[51] Int. Cl.[6] .................................................. A61B 17/16
[52] U.S. Cl. ............................................................ 606/80
[58] Field of Search ................................. 606/80, 79, 85, 606/84, 96

[56] References Cited

U.S. PATENT DOCUMENTS

| | | | |
|---|---|---|---|
| 4,830,000 | 5/1989 | Shutt | 606/80 |
| 5,443,468 | 8/1995 | Johnson | 606/80 |
| 5,759,185 | 6/1998 | Grinberg | 606/80 |

*Primary Examiner*—Michael Buiz
*Assistant Examiner*—David O. Reip
*Attorney, Agent, or Firm*—Todd A. Dawson

[57] ABSTRACT

A reamer for reaming a uniform opening in an intramedullary canal of a bone. The reamer has an impeller rigidly attached to the shaft of the reamer proximal to the reamer head. The impeller blades have a pitch higher than the pitch of the reamer head flutes. The increased pitch between the impeller blades and the reamer head flutes produces a partial vacuum while the unit is turning, pulling debris up and out of the bony canal and reducing pressure in the intramedullary canal.

7 Claims, 2 Drawing Sheets

BONE REAMER WITH IMPELLER

FIELD OF THE INVENTION

The present invention relates to reamers used for producing uniform passages in bone and in particular to a reamer having an impeller for removing debris from the passages formed during reaming.

BACKGROUND OF THE INVENTION

The intramedullary canal of a long bone, such as a femur, is filled with fat and marrow elements. It is necessary to produce uniform passages in long bones in order to admit fracture fixation devices such as intramedullary nails. Reaming is accomplished with a power unit attached to the reamer. The reamer produces bone chips during reaming. The fat, marrow elements and bone chips are pushed forward by the prior art reamers during reaming, thereby increasing the intramedullary pressure. Prior art reamers have reamer shafts that are similar in diameter to the reamer heads. The combination of diameters and the viscosity of the fat, marrow elements, and bone chips effectively plugs the intramedullary canal.

SUMMARY OF THE INVENTION

The present invention solves the problems of the prior art by including an impeller rigidly attached to the shaft of the reamer proximal to the reamer head. The impeller blades have a pitch higher than the pitch of the reamer flutes. The higher pitch of the impeller blades creates a partial vacuum in the intramedullary canal, pulling out the debris. The impeller can be made of a rigid material or of a flexible material. The impeller can consist of a single set of blades in one plane or several sets of blades arranged in turbine-like fashion on the shaft of the reamer. The impeller can have blades that are squared off on the tips or rounded as in the blades on a ship's propeller. The blades can be separate units or connected at the tips by a circumferential ring. Accordingly it is an object of the invention to provide a bone reamer having an impeller connected to the shaft and spaced from the reamer head. Another object of the invention is to provide a bone reamer wherein the debris formed by reaming is sucked or pulled away from the reamer head.

DETAILED DESCRIPTION OF THE INVENTION

The following descriptions of the preferred embodiment are not intended to be exhaustive, or to limit the invention to the precise form disclosed. Rather they are chosen in order to explain the invention so that one skilled in the art might utilize their teachings.

Figure 1:
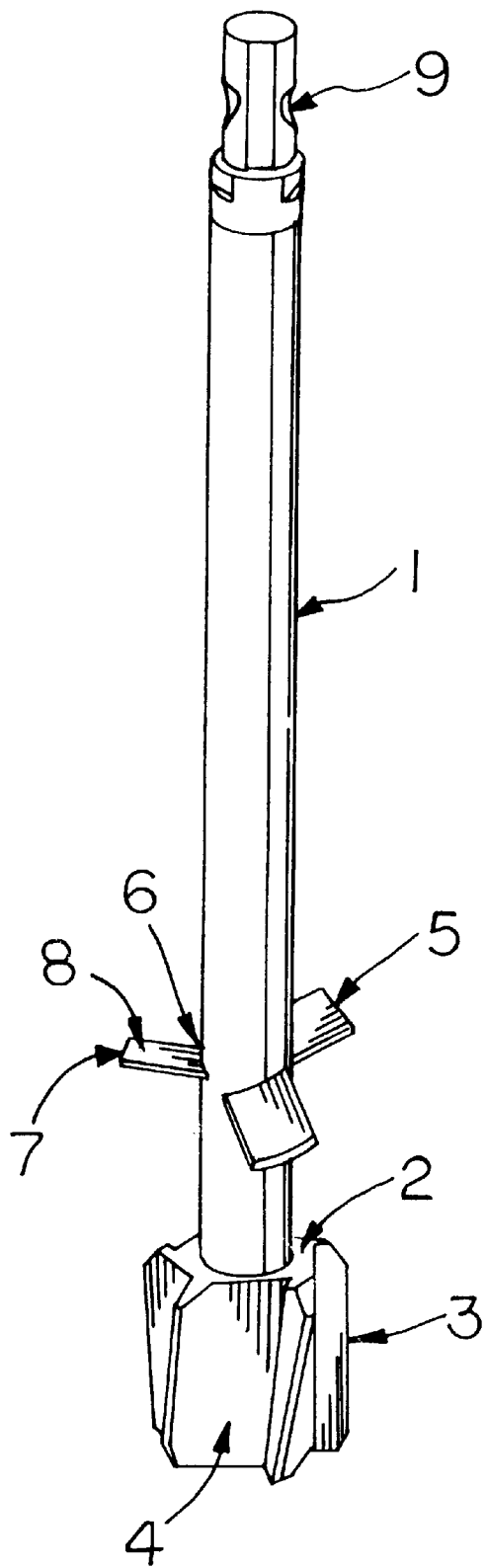
FIG. 1 is a side view of the reamer.
Figure 2:
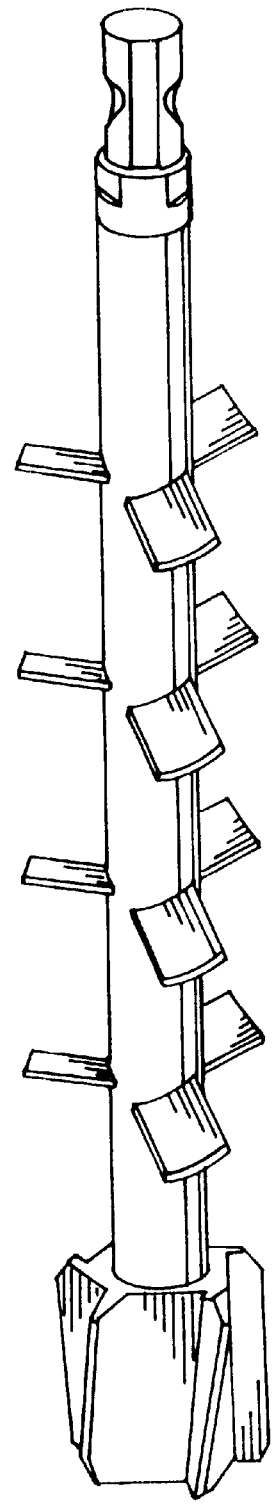
FIG. 2 is a side view of an alternative embodiment of the present invention.

FIG. 1 depicts one embodiment of the present invention. A reamer shaft 1 forms the body of the reamer. The ratio of the length of the shaft to the diameter of the shaft is greater than 1.0. A reamer head 2 is attached to one end of the reamer shaft. The reamer head is formed by a plurality of cutting flutes 3, each pair of flutes separated by a channel 4. An angle is formed by the plane of each cutting flute with the axis of the reamer shaft. The angle of the reamer flutes is referred to as the pitch of the reamer flutes. The angle of the reamer head cutting flutes plane relative to the axis of the reamer shaft is greater than 90°. An impeller 5 is attached to the reamer shaft 1 and spaced from the reamer head 2. The impeller is formed by having at least two blades, each blade having a first end 6 and a second end 7. The first end 6 of each blade is attached to the reamer shaft. The first end 6 and second end 7 of each blade are connected by a planar surface 8. The planar surface describes a plane relative to the longitudinal axis of the reamer shaft. The planes intersect the axis of the reamer shaft at an angle greater than 90°. The second end of each blade projects outwardly from the reamer shaft. The second end of each blade does not project outwardly farther than the outer diameter of the reamer head. The angle of the blade, defined by the angle of the planar surface formed by the connection between the first end and second end of the blade, relative to the longitudinal axis of the reamer shaft, is described as the pitch of the blades. The pitch of the blades is greater than the pitch of the reamer flutes. The opposite end of the reamer 9 is adapted to a known rotary driver(not shown). In the embodiment shown in FIG. 1, the impeller is formed of three blades attached to the reamer shaft. FIG. 2 depicts an embodiment of the invention wherein the impeller portion extends from the reamer head 2 to the opposite end 9 of the reamer in a turbine-like fashion. A plurality of impellers 5 spaced apart from the reamer head and from each other are attached to the reamer shaft The impeller can have rigid or flexible blades. The shape of the impeller blades can be square or rounded. The second ends 7 of the blades of the impeller can be connected by a ring passing around the circumference of the second ends 7 of the blades.

Figure 3:
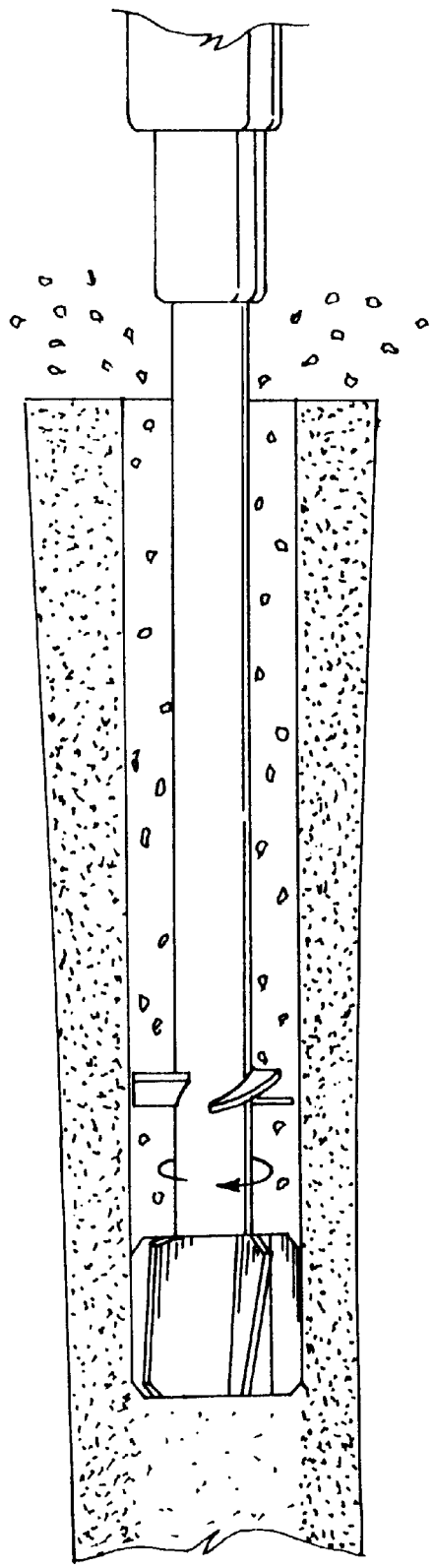
FIG. 3 is a cross section view of a bone during reaming with the present invention.

Referring now to FIG. 3, the function of the reamer will be explained. In use the reamer is rotated in the intramedullary canal of a long bone, such as a femur. The reamer head cuts the bone, producing chips and other debris. The chips and debris are collected by the channels formed between the flutes. The pitch of the reamer head flutes moves the debris toward the impeller. The impeller, being connected to the shaft, rotates with the shaft and reamer head. The pitch of the impeller blades also causes chips and debris to be collected between the blades and moved past the impeller. Since the pitch of the impeller blades is greater than the pitch of the reamer head flutes, a partial vacuum is formed between the reamer head and the impeller. The partial vacuum causes the chips and debris to be moved away from the reamer head to help reduce the intramedullary pressure. The pitch of the impeller blades relative to the pitch of the reamer head flutes is greater, thereby increasing the efficiency of chip and debris removal.

It should be understood that the invention is not to be limited to the precise forms disclosed. Rather, they may be modified within the scope of the appended claims.

What is claimed is:

1. An intramedullary reamer, said reamer including a shaft, said shaft having first and second ends, said first end being adapted for connection to a rotary driver, a reamer head is attached to the second end of said shaft, an impeller is connected to said shaft between said first and second ends, said impeller being spaced from said reamer head.

2. A reamer of claim 1 wherein said impeller, comprising at least two blades, each blade including a first end and a second end, said first end attached to said reamer shaft and second end projecting outwardly from the reamer shaft.

3. A reamer, as recited in claim 2, where said impeller is made of a rigid material.

4. A reamer, as recited in claim 2, where said blade second ends are connected by a circumferential ring.

5. A reamer of claim 2 wherein said impeller blades are connected at a first angle relative to said longitudinal axis of said shaft, said reamer head having cutting flutes which are formed at a second angle relative to said longitudinal axis of said shaft, wherein said first angle is greater than said second angle.

6. A reamer having a shaft with a first end and a second end, said first end being adapted for connection to a drive unit, said second end having a reamer head attached to said shaft; and a plurality of impellers attached to said shaft spaced from said reamer head and continuing toward said first end of said reamer shaft.

7. An intramedullary reamer, said reamer including a shaft, said shaft having first and second ends, said first end being adapted for connection to a rotary driver, a reamer head is attached to the second end of said shaft, an impeller is connected to said shaft between said first and second ends, wherein said impeller causes a negative pressure to be formed during rotation, said impeller being spaced from said reamer head, said impeller comprising at least two blades, each blade including a first end and a second end, said first end attached to said reamer shaft and said second end projecting outwardly from said reamer shaft.

* * * * *